(12) United States Patent
Rigler

(10) Patent No.: US 8,252,604 B2
(45) Date of Patent: Aug. 28, 2012

(54) SELECTION OF PARTICLES IN LAMINAR FLOW

(76) Inventor: Rudolf Rigler, Djursholm (SE)

( * ) Notice: Subject to any disclaimer, the term of this patent is extended or adjusted under 35 U.S.C. 154(b) by 1037 days.

(21) Appl. No.: 11/664,423

(22) PCT Filed: Sep. 29, 2005

(86) PCT No.: PCT/EP2005/010548
§ 371 (c)(1),
(2), (4) Date: Apr. 2, 2007

(87) PCT Pub. No.: WO2006/037561
PCT Pub. Date: Apr. 13, 2006

(65) Prior Publication Data
US 2008/0108143 A1    May 8, 2008

Related U.S. Application Data

(60) Provisional application No. 60/662,799, filed on Mar. 18, 2005.

(30) Foreign Application Priority Data

Oct. 1, 2004  (DE) .................. 10 2004 047 953

(51) Int. Cl.
*B03C 5/02* (2006.01)
*G01N 15/14* (2006.01)

(52) U.S. Cl. ...... 436/501; 422/50; 422/68.1; 422/82.05; 422/82.08; 435/308.1; 435/287.3; 204/643; 204/547

(58) Field of Classification Search .................. None
See application file for complete search history.

(56) References Cited

U.S. PATENT DOCUMENTS

| | | | |
|---|---|---|---|
| 6,582,903 B1 * | 6/2003 | Rigler et al. | 435/6 |
| 7,807,454 B2 * | 10/2010 | Oh et al. | 435/308.1 |
| 7,897,026 B2 * | 3/2011 | Chou et al. | 204/547 |
| 2003/0044832 A1 | 3/2003 | Blankenstein | |
| 2003/0159999 A1 * | 8/2003 | Oakey et al. | 210/695 |
| 2003/0170609 A1 | 9/2003 | Rigler | |
| 2007/0125941 A1 * | 6/2007 | Lee et al. | 250/251 |
| 2007/0151855 A1 * | 7/2007 | Schnelle et al. | 204/547 |
| 2007/0163883 A1 * | 7/2007 | Schnelle et al. | 204/547 |
| 2011/0020459 A1 * | 1/2011 | Achrol et al. | 424/520 |

FOREIGN PATENT DOCUMENTS

| | | |
|---|---|---|
| WO | WO 03/066191 A | 8/2003 |
| WO | WO 03/078972 A | 9/2003 |
| WO | WO 03/099440 A | 12/2003 |
| WO | WO 2007/092713 | * 8/2007 |

* cited by examiner

*Primary Examiner* — P. Kathryn Wright
(74) *Attorney, Agent, or Firm* — Rothwell, Figg, Ernst & Manbeck, P.C.

(57) ABSTRACT

The invention relates to a method for selecting charged particles possessing a predetermined property from a population of a multiplicity of different particles, and also to a device which is suitable for implementing the method.

21 Claims, 2 Drawing Sheets

SELECTION OF PARTICLES IN LAMINAR FLOW

CROSS REFERENCE TO RELATED APPLICATION

This application is a 35 USC §371 National Phase Entry Application from PCT/EP2005/010548, filed Sep. 29, 2005, designating the United States, which claims the benefit of U.S. Provisional 60/662,799, filed Mar. 18, 2005.

The invention relates to a method for selecting charged particles possessing a predetermined property from a population of a multiplicity of different particles, and also to a device which is suitable for implementing the method.

Combinatorial libraries, consisting of a population of a multiplicity of particles, e.g. phages, cells, ribosomes, etc., with the individual particles in each case presenting different ligands, can be used for identifying new ligands for diagnostic, biomedical and pharmaceutical applications (see, e.g., WO 90/02809; WO 92/15677; WO 92/15679; WO 92/06204; WO 92/06176; WO 98/19162; WO 98/35232; WO 99/06839 and WO 99/5428). In order to identify ligands possessing a predetermined property, the library to be investigated is normally screened, with a labeled target molecule being brought into contact with the individual particles in the library and the occurrence of a bond between the target molecule and a particular particle in the library, or the ligand presented by the particle being determined. The particle possessing the predetermined property has then to be identified. However, previous selection and identification methods, e.g. the methods known as panning or selex, are of relatively low efficiency, which means that a particular particle possessing desired properties may frequently not be found in the library even though it is in fact present.

The method of fluorescence correlation spectroscopy (FCS), which is described in European Patent 0 679 251, has been reported to directly detect individual analyte molecules. FCS can be used to detect a single, or only a few, fluorescent dye-labeled molecule(s) in a small measurement volume of, for example, $<10^{-14}$ l. The FCS measurement principle is based on a small volume element of the sample liquid being subjected to a powerful excitation light, e.g. of a laser, such that only those fluorescent molecules which are present in this measurement volume are excited. The fluorescent light which is emitted from this volume element is then imaged on a detector, e.g. a photomultiplier. A molecule which is located in the volume element will once again leave the volume element, in accordance with its characteristic diffusion rate and in a time which is a mean time but which is characteristic for the molecule concerned, and then no longer be observable.

If the luminescence of one and the same molecule is now excited several times during the mean dwell time of the molecule in the measurement volume, many signals can be collected from this molecule.

The use of fluorescence correlation spectroscopy for sorting and identifying individual molecules is described in Eigen and Rigler (Proc. Natl. Acad. Sci. USA 91 (1994), 5740-5747) and Rigler (J. Biotech. 41 (1995), 177-186). The authors propose the use of a quadrupole trap and electric field gradients in combination with single photon detectors for identifying individual molecules.

WO 02/01189 discloses a method for selecting particles in several cycles, with the particles being conveyed, in each cycle, in a microchannel through a detection element which can distinguish between labeled and unlabeled particles and the concentration of the particles being reduced in a subsequent cycle as compared with the preceding cycle.

Since known methods are time-consuming and elaborate, there is a need to further improve the sensitivity and efficiency when selecting particles.

This problem is solved by a method and a device for selecting charged particles possessing a predetermined property with the method and device being based on charged particles which carry a detectable label, being conveyed, in a first laminar fluid stream, through a channel and being transferred by means of an electric field pulse of predetermined magnitude (voltage and duration) from the first laminar fluid stream into a concurrent adjacent laminar fluid stream without substantial fluid volumes being exchanged between the fluid streams. In this way, labeled particles can be selectively removed from the first fluid stream and thereby separated from unlabeled particles.

A subject matter of the invention is consequently a method for selecting a particle possessing a predetermined property from a population encompassing a multiplicity of different particles, comprising the steps of:
 (a) providing a population of different particles,
 (b) labeling particles which possess a predetermined property,
 (c) conveying a first fluid stream, which contains the particles and under conditions under which the particles carry an electric charge, through a channel, with the first fluid stream being in contact with at least one second fluid stream which is flowing concurrently, essentially without mixing, with the first fluid stream,
 (d) conveying the fluid streams through a detection element which is able to distinguish between labeled and unlabeled particles,
 (e) separating off a detected labeled particle by applying an electric field in order to transfer the particle from the first fluid stream into a second fluid stream, and
 (f) identifying and/or characterizing the labeled and separated-off particle where appropriate.

The invention furthermore relates to a device for selecting a particle possessing a predetermined property from a population encompassing a multiplicity of different particles, comprising:
 (a) a channel in which a first and at least one second fluid stream are able to flow concurrently, in contact with each other and essentially without mixing,
 (b) means for introducing a first fluid stream into the channel, with the first fluid stream containing the particles and the particles carrying an electric charge,
 (c) means for introducing at least one second fluid stream into the channel,
 (d) means for detecting a label on a charged particle which is conveyed through the channel in the first fluid stream, and
 (e) means for separating off a detected labeled particle from unlabeled particles, with the means comprising means for applying an electric field in order to transfer the particle from the first fluid stream into a second fluid stream.

DETAILED DESCRIPTION OF THE INVENTION

Figure 1:
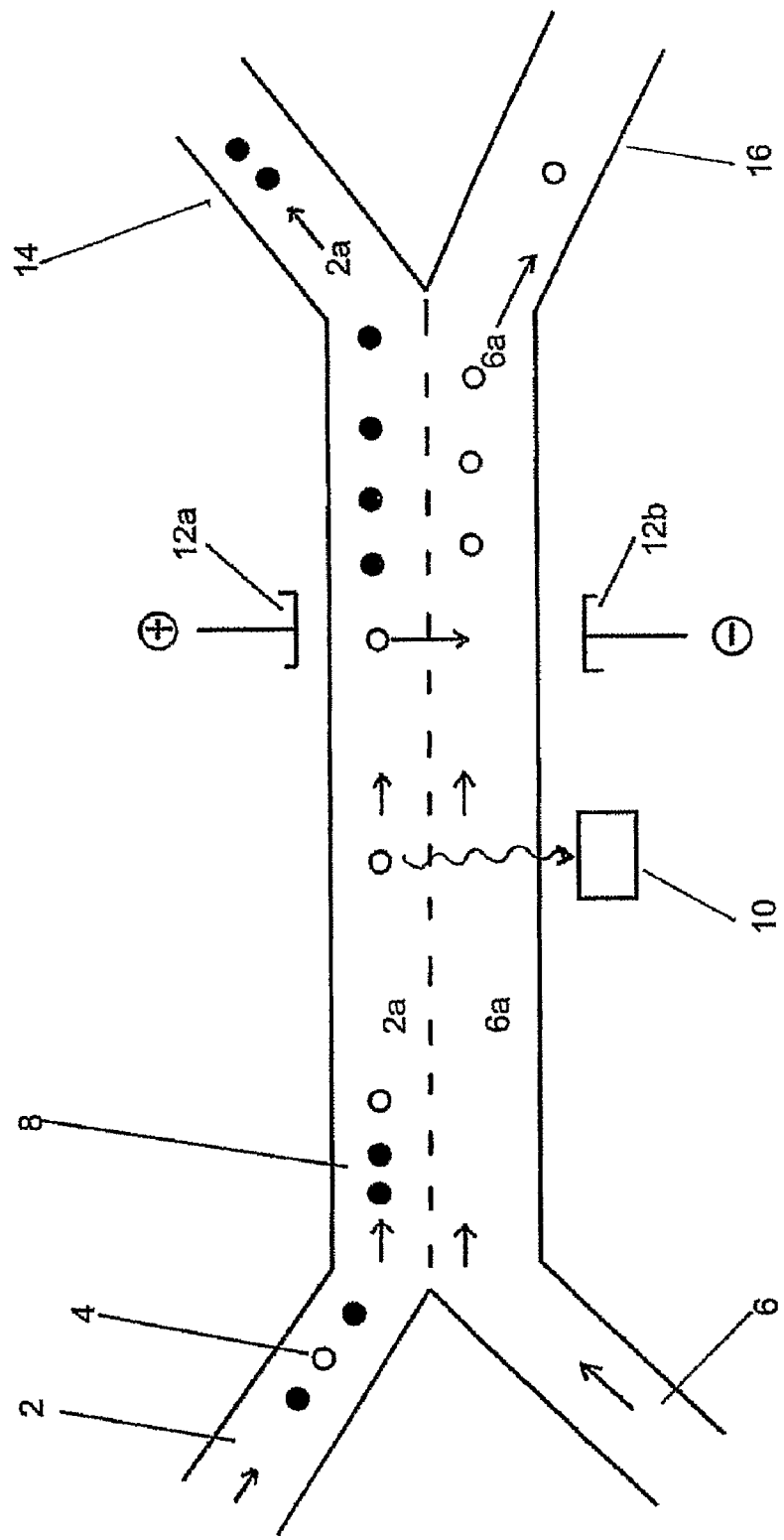
FIG. 1 is a schematic diagram of a first embodiment of a device for carrying out the method according to the invention.

The method according to the invention makes it possible to select individual particles from very large particle populations which comprise, for example, more than $10^8$ or even $10^{12}$ or more different particles. The particles possess an electric charge, i.e. an overall positive or negative electric charge, such that, as a result of applying an electric field essentially perpendicular to the direction of flow, they are able to migrate in the electric field in accordance with their charge and are consequently able to be transferred from the first fluid stream into a second fluid stream. Examples of particles are cells, parts of cell surfaces, cell organelles, e.g. ribosomes, viruses such as bacteriophages, e.g. filamentous phages or plasmids packaged in phage envelopes (phagemids), nucleic acids such as genes or cDNA molecules, proteins such as enzymes or receptors, or low molecular weight substances. The particles are preferably elements of a combinatorial library, e.g. a library of genetic packages such as phages, cells, spores or ribosomes, which present peptide structures, e.g. linear or circular peptides, or proteins such as antibodies, preferably fused to surface proteins, e.g. surface proteins of filamentous phages on their surface. The particles can also be elements of a chemical library.

The method according to the invention makes it possible to efficiently select a particle possessing a predetermined property from a multiplicity of different particles. Within the meaning of the present invention, "predetermined property" is preferably to be understood as meaning the ability to bind to a target substance. The binding of the particle to the target substance can comprise a ligand-receptor bond, an enzyme-substrate bond, an antibody-antigen bond, a nucleic acid hybridization, a sugar-lectin bond or another high-affinity biological or chemical interaction. On the other hand, the predetermined property of the particle can also consist in preventing a biological or chemical interaction, for example binding to a target substance.

In order to select the particle possessing the predetermined property, the particle population is preferably incubated with a target substance carrying a detectable label, with the incubation conditions being selected such that the particle possessing the predetermined property binds to a labeling group and can in this way be separated off from other particles. Suitable labeling groups are, in particular, nonradioactive labeling groups and particularly preferred, labeling groups which can be detected by optical methods, such as dyes, and, in particular, quantum labeling groups or fluorescent labeling groups. Examples of suitable fluorescent labeling groups are rhodamine, Texas red, phycoerythrin, fluorescein and other fluorescent dyes which are customary in diagnostic methods or selection methods.

The labeled target substance is specific for the particle to be identified, i.e. the target substance binds under test conditions to the particle possessing the predetermined property with an affinity and selectivity which are sufficiently high to enable selection to take place.

Where appropriate, the predetermined property of the particle to be selected can also be a biological activity, e.g. an enzymic activity. In this case, the particles can be incubated with a chromogenic or fluorescent enzyme substrate and encapsulated in vesicles, e.g. lipid vesicles such as liposomes or vesicles composed of amphiphilic block copolymers. If a particle, e.g. a phage or a ribosome, is presenting an active enzyme molecule at its surface, the substrate is reacted within the vesicle, with a colored or fluorescent product, which can be detected being formed.

In a preferred embodiment of the method according to the invention, an affinity preselection procedure is undertaken after the particles have been labeled but before the particles have been introduced into the detection device. In this case, after the particle population has been labeled, for example by being treated with a labeled binding molecule, a further treatment step is carried out using unlabeled binding molecules such that the labeled binding molecule can be replaced, by means of dissociation, with the unlabeled binding molecule in the case of particles which have only bound the labeled binding molecule weakly. In this case, these particles which are only able to bind weakly, and which are consequently unwanted, are recognized from the outset of the selection procedure as not being positive and are therefore eliminated. The "stringency" of the affinity preselection can be adjusted by adjusting the conditions when treating labeled particles with unlabeled binding molecules. An increase in the stringency is achieved by increasing the duration of the incubation, the temperature and the concentration of unlabeled binding molecules.

If the predetermined property of the particle consists in selectively binding to a target substance, but, if possible, not binding to a substance which is closely related to the target substance, i.e. an analog of the target substance, an incubation with the closely related substance can be effected before and/or after the labeling of the target substance such that particles having an affinity for the closely related substance are from the outset not detected in the selection procedure.

A preferred example of a population of charged particles is a combinatorial library of genetic elements, such as a ribosome library, with individual elements of this library containing a population of different proteins, e.g. antibodies, enzymes or nucleic acid binding proteins, such as transcription factors, a nucleic acid, e.g. an mRNA, encoding the respective protein and a ribosome (cf. e.g. Hanes et al., Proc. Natl. Acad. Sci. USA 95 (1998), 14130-14135). The ribosome library is preincubated with a ligand, which, as target substance, carries a label for the protein, with only proteins having a predetermined selectivity or affinity binding to the labeled ligand in accordance with the incubation conditions. Where appropriate, an incubation with an excess of unlabeled ligand and/or a ligand analog can then take place such that labeled ligands are displaced from the proteins when the bond is of low affinity or low selectivity. In this way, complexes of higher or lower affinity or selectivity can be obtained depending on the duration of the incubation with the unlabeled ligand or ligand analog. Another preferred example is constituted by vesicles which contain enzymes or other catalytic molecules, e.g. catalytic antibodies, and in which, when the selected catalytic activity is present, labeled products are formed, e.g. as a result of using fluorogenic substrates for the catalytic reaction. The vesicles contain positive or negative charge carriers on their surface, e.g. as a result of incorporating positively or negatively charged lipids into the vesicle membrane.

In order to differentiate labeled particles, i.e. particles possessing the predetermined property, and unlabeled particles, i.e. particles without the predetermined property, the fluid stream containing the particles is conveyed through a detection element. At least one second fluid stream is conveyed through the channel, in contact with the first fluid stream and in the same direction of flow, with the fluid streams flowing through the channel essentially without mixing and preferably in each case in laminar flow.

The flows are preferably conveyed through the channel by hydrodynamic means, for example by a suction or pumping effect. However, the flows can also be generated by electroosmotic means, for example by electric field gradients. It is furthermore possible to combine hydrodynamic flow and field gradients. The flows through the channel preferably exhibit a parabolic flow profile, i.e. the flow rate is maximal in the center of the respective fluid stream and decreases, in a parabolic function, down to a minimal rate at the edges. The maximum rate of flow through the channel is preferably in the range from 1 to 100 mm/s, particularly preferably in the range of from 5 to 10 mm/s. The diameter of the channel is preferably in the range from 1 to 500 µm, particularly preferably of from 10 to 100 µm. The fluid streams are preferably conveyed through a linear channel having an essentially constant diameter.

The first fluid stream and the at least one second fluid stream are preferably in each case conveyed into the channel through separate inlets. Preference is furthermore given to the first and the at least one second fluid stream in each case being conveyed away from the channel through separate outlets. In addition to the first fluid stream, several second fluid streams, e.g. 2 second fluid streams, are preferably conveyed through the channel. The first fluid stream, which contains the charged particles, is preferably in contact with at least 2 other fluid streams. In this connection, the flow rate in the first fluid stream is advantageously lower than the flow rate in the at least one second fluid stream, with there preferably being a 2-10-fold difference in the rates in the fluid streams.

The first fluid stream, containing the particles, and the other fluid streams are conveyed through a detection element. A labeled particle can be identified by means of any arbitrary measurement method, for example by means of a site-resolved and/or time-resolved fluorescence spectroscopy which is able to detect in a very small volume element as is present in a microchannel very small labeling group signals, in particular fluorescence signals, all the way down to single photon counting. In this connection, it is important that the signals originating from labeled particles are detected clearly such that it is possible to reliably distinguish these particles from the unlabeled particles.

For example, the detection can be carried out by means of confocal single molecule detection including single-molecule correlation spectroscopy and/or fluorescence correlation spectroscopy, in which a very small confocal volume element, for example from 0.1 to $20 \times 10^{-15}$ l, of the sample liquid flowing through the microchannel is subjected to the excitation light from a laser, which light excites the receptors which are present in this measurement volume to emit fluorescent light, with the emitted fluorescent light from the measurement volume being measured by means of a photodetector and a correlation being generated between the temporal change in the measured emission and the relative flow rate of the molecules involved such that at an appropriately high dilution, individual molecules can be identified in the measurement volume. For details with regard to the implementation of the method and technical details with regard to the equipment employed for the detection, the reader is referred to the disclosure in European patent 0 679 251.

Alternatively, the detection can also be effected by means of dynamic time-resolved analysis methods, e.g. a time-resolved decay measurement, what is termed a time gating as described, for example by Rigler et al., "Picosecond Single Photon Fluorescence Spectroscopy of Nucleic Acids", in: "Ultrafast Phenomenes", D. H. Auston, Ed., Springer 1984. In this method, the fluorescent molecules are excited within a measurement volume and, after that, preferably after a time interval of $\geqq 100$ ps, a detection interval is opened in the photodetector. In this way, it is possible to keep background signals generated by Raman effects small enough for the detection to be essentially interference-free.

Particularly preferably, the device for detecting fluorescence-labeled particles in the sample liquid flowing through the channel comprises a laser, as the fluorescence excitation light source for the molecules, and an optical arrangement for conducting and focusing laser light from the laser on a focal region of the channel and for confocally imaging the focal region on a photodetector arrangement for detecting fluorescent light which has been emitted, in the focal region, by one or, where appropriate, several optically excited molecules, with the optical arrangement possessing a diffraction element or a phase-modulating element in the beam path of the laser, which element is arranged where appropriate in combination with one or more optical imaging elements to generate a diffraction pattern in the form of a linear or two-dimensional array of focal regions in the microchannel from the laser beam of the laser, with the optical arrangement being arranged to image each focal region confocally for the fluorescence detection by the photodetector arrangement. Alternatively, the detection device can possess two walls which border the channel on opposing sides, one of which walls exhibits an array of laser elements, as fluorescence excitation light sources, which are preferably integrated and which emit into the channel, and the other of which walls exhibits an array of photodetector elements, as fluorescent light detectors, which are preferably integrated and are assigned to the laser elements which are in each case facing them, with the laser elements preferably being potential well laser elements and the photodetector elements being avalanche diodes. Devices of this nature are described, for example in WO 01/86285.

The particles which are identified by the detection element, and which carry a label, are separated off from unlabeled particles. To do this, if the detection element recognizes a labeled particle, an electric field is laid over the channel downstream in the direction of flow in order to transfer the labeled charged particles from the first fluid stream into another fluid stream. The electric field is preferably generated by means of electrodes which are arranged at and/or in the walls of the channel. In this connection, the electrodes can be located within the channel or be integrated in the channel walls. An electrode arrangement comprising two wire electrodes, for example composed of Pt, which are arranged at opposing walls of the channel in the interior of the channel has, for example proved to be suitable. Since the particles are being transported in the fluid stream through the channel while the electric field is being applied, the electrodes preferably possess a lateral extent of from 1 to 10 mm in order to maintain the electric field for a period of time which is sufficient to enable the labeled, charged particle to be transferred from the first fluid stream into a second fluid stream.

The period of time for which the electric field is applied follows from the migration rate of the particles and the distance to be covered transverse to the direction of flow. The migration rate of the charged particles in the electric field is determined by the field strength and the total charge and size of the particles. The distance follows from the diameters of the fluid streams. Good results can be achieved, for example, if the electric field is applied for a period of 20-200 ms and with a voltage of 10-50 V. Preferably, the parameters in connection with applying the electric field are adjusted such that the labeled particle is, if possible at all, transported into a central region of the second fluid stream. More detailed information on the migration of particles in an electric field can be found in Rigler, Electrophoresis 23 (2002), 605-608.

The transfer of the labeled particle from the first fluid stream into the second fluid stream brings about a spatial separation of the labeled particles from unlabeled particles without there being any significant exchange of fluid between the fluid streams. The second fluid stream, which now contains the labeled particles, is then preferably separated off from the first fluid stream, for example by the first and second fluid streams in each case being conveyed away from the channel through separate outlet apertures. The particles which are present in the second fluid stream can then be subjected to an analysis.

This analysis preferably comprises identifying and/or characterizing the particles possessing the predetermined property which have been found. This step can, for example comprise an amplification, for example a propagation in the case of cells and viruses or an amplification reaction such as PCR, or a sequencing in the case of nucleic acids. The identified or characterized particle, or its characteristic determinant, e.g. a protein which is presented on the surface can then be used for the purpose which is in each case envisaged for it, or employed as the basis for preparing a further combinatorial library, e.g. by means of mutagenesis.

The selection procedure according to the invention can be carried out in a cycle or in several consecutive cycles, in connection with which it is possible to reduce the number of particles which are falsely identified as being positive. Such a procedure is described, for example in WO 02/01189.

A preferred device for implementing the method according to the invention contains:
(i) a first inlet for introducing the first fluid stream, which contains the particles which are to be selected and which carry an electric charge,
(ii) one or more second inlets for introducing at least one second fluid stream,
(iii) a channel in which the inlets (i) and (ii) open out into and which is configured such that the first and second fluid streams flow concurrently in it, in contact with each other and essentially without mixing,
(iv) several outlets for separately conveying away the fluid streams from the channel,
(v) a detection element for recognizing labeled particles, and
(vi) means for applying an electric field, for example electrodes, in order to transfer charged particles from the first fluid stream into one of the second fluid streams.

Preferably, the device according to the invention contains at least two separate supply lines for introducing 2 second fluid streams. In this connection, the supply lines are arranged such that the first fluid stream is conveyed through the channel in contact with the two other fluid streams.

The device preferably also contains automatic manipulation devices, heating or cooling devices, such as Peltier elements, reservoirs and/or electronic analytical equipment.

The device is particularly suitable for carrying out the method according to the invention.

The invention will also be explained by means of the following figures:

FIG. 1 is a diagram of a first embodiment of a device for carrying out the method according to the invention. A population of labeled (empty circles) and unlabeled (filled circles) particles (4) is introduced in a first fluid stream (2a) into the device through a first inlet (2). A second inlet (6) serves for introducing a second fluid stream (6a). The first and second inlets (2, 6) open out into a channel (8) in which the first fluid stream (2a) originating from the first inlet (2) flows concurrently with the second fluid stream (6a) originating from the second inlet (6), without mixing, preferably in each case in a laminar flow. The diameters of the inlets (2, 6) are preferably in the range of approx. 1-5 mm. The channel (8) preferably has a width of 50 μm and a depth of 20 μm. However, the shapes and dimensions of the inlets and/or of the channel can be varied substantially provided they ensure a mixing-free flow of several separate fluid streams. Where appropriate, the inlets can also serve as reservoir volumes.

A detection element (10), preferably a confocal detection element, is arranged in the region of the channel (8), with the element recognizing the labeled particles which are being transported through the channel (8) in the first fluid stream (2a), for example by means of intercepting a signal, for example an optical signal such as a fluorescence emission signal, which originates from the label. The signal can be generated by corresponding excitation with a light source, for example a laser (not shown). An electrode arrangement having a positive electrode (12a) and a negative electrode (12b) is located downstream of the detection element. By means of applying an electric field in the region of the electrodes (12a, 12b), positively charged particles are transferred from the first fluid stream (2a) into the second fluid stream (6a). (When the polarity of the electrodes (12a, 12b) is reversed, negatively charged particles can in a corresponding manner be transferred from the first fluid stream (2a) into the second fluid stream (6a). Controlling the time and the period for applying the electric field in the region of electrodes (12a, 12b) makes it possible to transfer labeled particles selectively into the second fluid stream (6a) while unlabeled particles remain in the first fluid stream (2a).

Downstream of the electrode arrangement (12a, 12b), the channel (8) divides into a first outlet (14) and a second outlet (16). Whereas the unlabeled particles, which have remained in the first fluid stream (2a), are conveyed away from the device through the first outlet (14), the labeled particles are separately conveyed away in the second fluid stream (6a) through the second outlet (16). The diameters of the outlets preferably correspond to the diameters of the inlets.

Figure 2:
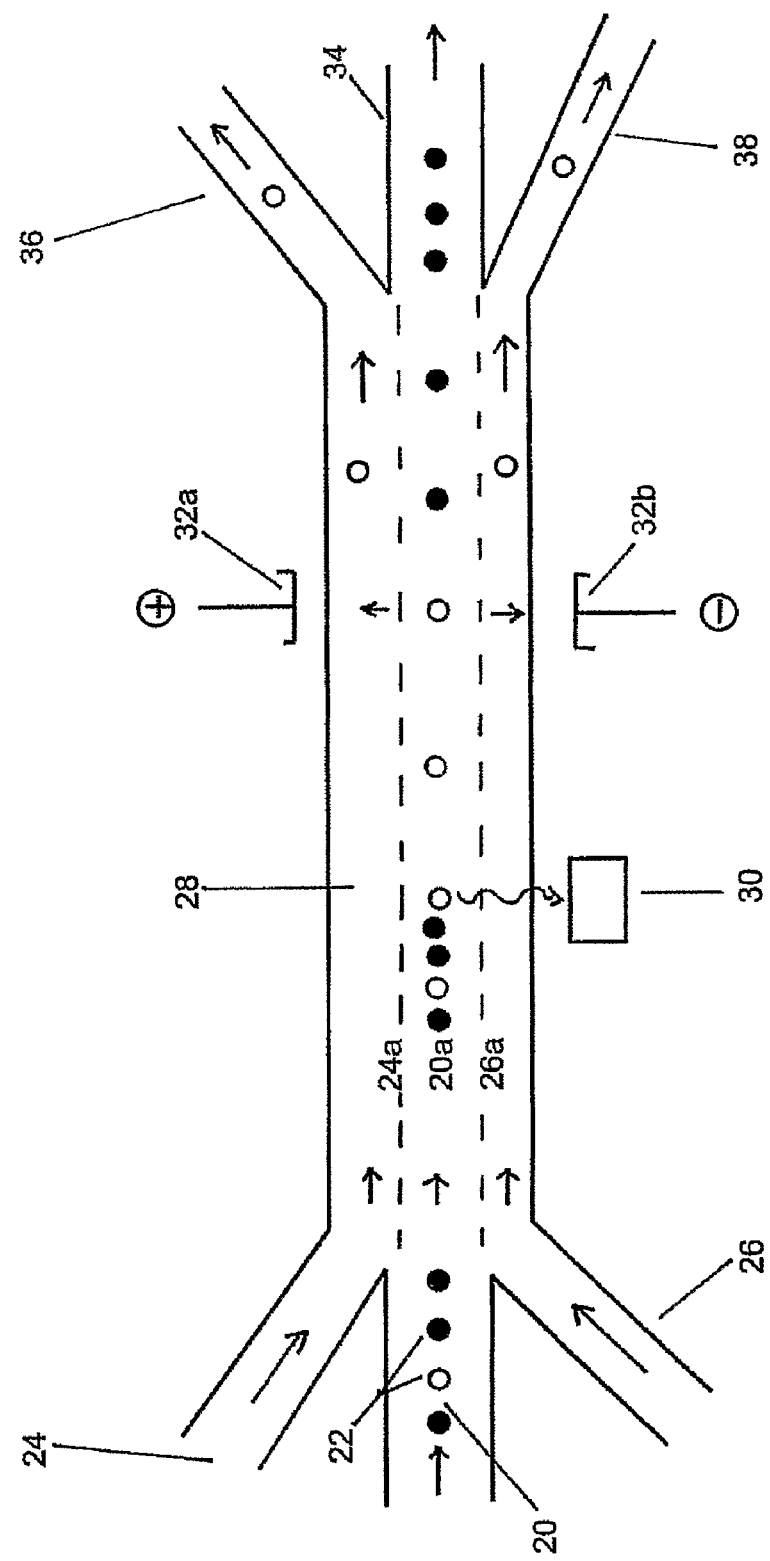
FIG. 2 is a schematic diagram of a second embodiment of a device for carrying out the method according to the invention.

FIG. 2 is a diagram of a second embodiment of a device for carrying out the method according to the invention. This device contains a first inlet (20) for introducing a first fluid stream (20a) which contains the particles (22) to be selected, with labeled particles (empty circles) and unlabeled particles (filled circles) being present. The device furthermore contains two inlets (24, 26) for introducing two further "second" fluid streams (24a, 26a). The inlets (22, 24, 26) open out into a channel (28) in which the fluid streams (20a, 24a, 26a) flow concurrently, and without mixing, alongside each other, preferably in laminar flow, without any mixing of the fluid streams taking place. A detection element (30), preferably a confocal detection element, which is arranged in the region of the channel (28) recognizes a labeled particle on the basis of signals which originate from the label. An electrode arrangement (32a, 32b) having a positive and a negative electrode is located downstream of the detection element. By means of applying an electric field in the region of the electrode arrangement, labeled particles are transferred in accordance with their charge from the first fluid stream (20a) into one of the two second fluid streams (24a, 26a). In the device which is depicted, the particles having a negative charge are transferred into the fluid stream 24a while those having a positive charge are transferred into the fluid stream 26a. Three outlets (34, 36, 38) are located at the end of the channel (28). The outlet (34) serves for conveying away the first fluid stream (20a), which still contains the unlabeled particles. The discharge lines (36, 38) serve for conveying away the fluid streams 24a and, respectively, 26a in which the labeled particles are present in accordance with their charge.

The invention claimed is:

1. A method for selecting a particle possessing a predetermined property from a population encompassing a multiplicity of different particles, comprising the steps of:
   (a) providing a population of different particles,
   (b) labeling particles which possess a predetermined property, (c) conveying a first fluid stream, which contains the particles and under conditions under which the particles carry electric charges, through a channel, with the first fluid stream being in contact with at least two additional fluid streams which are flowing concurrently, essentially without mixing, with the first fluid stream, (d) conveying the fluid streams through a detection element which is able to distinguish between labeled and unlabeled particles, (e) applying a negative field in order to transfer positively charged particles from the first fluid stream into a fluid stream conveying particles to a second outlet, (f) applying a positive field in order to transfer negatively charged particles from the first fluid stream into a fluid stream conveying particles to a third outlet, (g) conveying the fluid streams through three outlets for separately conveying away the fluid streams from the channel, wherein a first outlet conveys the first fluid stream, which still contains unlabeled particles, said second outlet conveys a fluid stream comprising particles having positive charge and said third outlet conveys a fluid stream comprising particles having negative charge, and (h) where appropriate identifying and/or characterizing the labeled and separated-off particle, wherein the population comprises more than $10^8$ different particles and the labeled particles are detected by confocal single molecule detection or dynamic time-resolved analysis.

2. The method as claimed in claim 1, wherein the particles are selected from cells, parts of cell surfaces, cell organelles, viruses, nucleic acids, proteins and low molecular weight substances.

3. The method as claimed in claim 1, wherein the population comprises a combinatorial library.

4. The method as claimed in claim 3, wherein the combinatorial library is selected from genetic packages such as phages, cells, spores or ribosomes or vesicles containing catalytically active proteins.

5. The method as claimed in claim 1, wherein the population comprises more than $10^{12}$ different particles.

6. The method as claimed in claim 1, wherein the labeling comprises incubating the particles with a target substance which carries a detectable label.

7. The method as claimed in claim 6, wherein the label employed is a fluorescent labeling group.

8. The method as claimed in claim 1, wherein the particles are conveyed through a channel having a diameter of from 1 to 500 microns.

9. The method as claimed in claim 1, wherein the first fluid stream and the at least two additional fluid streams are in each case conveyed into the channel through separate inlets.

10. The method as claimed in claim 1, wherein the first fluid stream and the at least two additional fluid streams are in each case conveyed out of the channel through separate outlets.

11. The method as claimed in claim 1, wherein the fluid streams exhibit a laminar flow.

12. The method as claimed in claim 1, wherein the flow rate in the fluid streams is in the range of 1-50 mm/s.

13. The method as claimed in claim 1, wherein the flow rate in the first fluid stream is lower than the flow rate in the at least two additional fluid streams.

14. The method as claimed in claim 1, wherein said particles are detected by confocal single molecule detection which is single-molecule correlation spectroscopy or fluorescence correlation spectroscopy.

15. The method as claimed in claim 1, wherein the electric field is generated by electrodes which are arranged at the walls of the channel.

16. The method as claimed in claim 1, wherein the electrodes exhibit a lateral extent of from 1 to 10 mm.

17. The method as claimed in claim 1, wherein the electric field is applied for a period of 20-200 ms.

18. The method as claimed in claim 1, wherein the electric field is generated by applying a voltage of 10-50 V.

19. The method as claimed in claim 1, wherein several consecutive selection cycles are carried out.

20. The method of claim 1, wherein said particles are detected by dynamic time-resolved analysis which is a time-resolved decay measurement.

21. The method of claim 20, wherein said time-resolved decay measurement includes time gating.

* * * * *